US012702363B2

(12) United States Patent
Ritschl

(10) Patent No.: US 12,702,363 B2
(45) Date of Patent: Aug. 11, 2026

(54) METHOD AND APPARATUS FOR GENERATING A RESULT IMAGE BASED ON A TOMOSYNTHESIS IMAGE DATASET OF A BREAST

(71) Applicant: Siemens Healthineers AG, Forchheim (DE)

(72) Inventor: Ludwig Ritschl, Buttenheim (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 151 days.

(21) Appl. No.: 18/827,916

(22) Filed: Sep. 9, 2024

(65) Prior Publication Data

US 2025/0082282 A1 Mar. 13, 2025

(30) Foreign Application Priority Data

Sep. 11, 2023 (EP) .................................... 23196632

(51) Int. Cl.

| | |
|---|---|
| ***A61B 6/02*** | (2006.01) |
| ***A61B 6/00*** | (2024.01) |
| ***A61B 6/04*** | (2006.01) |
| ***A61B 6/50*** | (2024.01) |

(52) U.S. Cl.

CPC ............ *A61B 6/025* (2013.01); *A61B 6/0414* (2013.01); *A61B 6/502* (2013.01); *A61B 6/5205* (2013.01)

(58) Field of Classification Search

CPC ........ A61B 6/025; A61B 6/0414; A61B 6/502
See application file for complete search history.

(56) References Cited

U.S. PATENT DOCUMENTS

| | | | | |
|---|---|---|---|---|
| 7,082,184 | B2 * | 7/2006 | Tsujii | A61B 6/025 378/21 |
| 7,444,011 | B2 * | 10/2008 | Pan | G06T 12/20 378/4 |
| 9,613,440 | B2 * | 4/2017 | Claus | G06T 12/20 |
| 12,288,275 | B2 * | 4/2025 | Bismuth | A61B 6/025 |
| 2009/0087067 | A1 * | 4/2009 | Khorasani | A61B 6/03 382/132 |
| 2015/0305705 | A1 * | 10/2015 | Goodenough | A61B 6/583 378/207 |
| 2021/0113169 | A1 | 4/2021 | Stango et al. | |
| 2025/0082282 | A1 * | 3/2025 | Ritschl | A61B 6/025 |

OTHER PUBLICATIONS

Sechopoulos, Ioannis et al; "Mammography and Digital Breast Tomosynthesis: Technique"; Breast Imaging: Diagnosis and Intervention; published: Nov. 2022; XP093132932; ISSN: 0942-5373; ISBN: 078-3-030- 94918-1.

* cited by examiner

*Primary Examiner* — David J Makiya

(74) *Attorney, Agent, or Firm* — Harness, Dickey & Pierce, P.L.C.

(57) ABSTRACT

The method for generating a resultant image comprises: defining curved slices between a compression plate and a detector, each curved slice having a shape that follows a curvature of the compression plate and/or detector or that represents a transition between the curvatures; reconstructing slice images that lie on the curved slices; generating the resultant image as a slice stack of the slice images; and outputting the resultant image.

20 Claims, 2 Drawing Sheets

METHOD AND APPARATUS FOR GENERATING A RESULT IMAGE BASED ON A TOMOSYNTHESIS IMAGE DATASET OF A BREAST

CROSS-REFERENCE TO RELATED APPLICATION(S)

The present application claims priority under 35 U.S.C. § 119 to European Patent Application No. 23196632.6, filed Sep. 11, 2023, the entire contents of which is incorporated herein by reference.

FIELD

One or more example embodiments of the present invention relate to a method and an apparatus for generating a result image based on a tomosynthesis image dataset of a breast and a corresponding mammography system. One or more example embodiments of the present invention are in particular concerned with non-planar post-processing of spectral X-ray images.

BACKGROUND

When examining the female breast, tomosynthesis is an advantageous technique for creating three-dimensional images. Typically, digital breast tomosynthesis reconstructs a cubic volume above the detector in which the breast lies. The height of the volume is typically defined by the compression thickness of the breast.

The cubic volume contains planar sections through the breast. Herein, the reconstruction can take place in such a way that the planar sections are reconstructed within the volume into a perspective coordinate system. This perspective coordinate system assists scanning along the spatially varying direction in Z-resolution, which is a key feature of DBT reconstruction. During this scanning, each beam can typically be parameterized with two angles $\alpha$ and $\varphi$ relative to the normal vector of the detector (Z-axis).

In the case of a curved compression paddle or an alternative compression or fixation method that preserves the natural curved shape of the breast, this reconstruction with planar sections leads to sub-optimal depiction of DBT sections that only show smaller parts of the breast in the outer sections.

SUMMARY

It is an object of one or more embodiments of the present invention to disclose an improved method and an improved apparatus for generating a result image based on a tomosynthesis image dataset of a breast with which the above-described disadvantages are avoided and which in particular enables non-planar post-processing of spectral X-ray images.

At least this object is achieved by a method, an apparatus and a mammography system as claimed and disclosed.

The method, according to an embodiment of the present invention, is used to generate a result image based on a tomosynthesis image dataset of a breast which has been fixed to a detector by a compression plate. Herein, a contact surface of the compression plate and/or detector facing the breast has a concave curvature. Therefore, the breast is not held between two flat plates and thus pressed to form a planar surface at the top and bottom, but has a curvature at the top and/or bottom. Since the plates are concavely curved, the breast held between them is convexly curved.

The method comprises the following steps:

- defining curved slices between the compression plate and detector, which follow the curvature of the compression plate and/or detector in their shape or represent a transition between these curvatures,
- reconstructing (curved) slice images that lie on the curved slices,
- generating the result image as a slice stack of the (curved) slice images,
- outputting the result image.

Therefore, the breast is held on the detector by the compression plate during recording. At least one of these two surfaces that compress the breast is concavely curved. This means that this surface allows a convex curvature of the breast. A concave curvature can, for example, be achieved in that the compression plate is bent downward at the edges, like a bowl, or in that it has a flat plate with a convex recess on its underside. However, the surface over the detector can also have a hollow. Therefore, the upper side and/or the underside of the breast being recorded is convexly curved.

Curved slices are now defined between the compression plate and detector according to the curvature of the breast, which corresponds in shape to the curvature of the compression plate and/or detector. These follow the curvature of the breast or represent a transition between different curvatures. It is preferable for the outermost slices to substantially follow the curvature of the breast in their shape, wherein "substantially" corresponds to at least 80%, in particular at least 90%. The intermediate slices should represent a (in particular regular) transition between the curvatures of the outermost slices.

Basically, two cases can be distinguished here: in one case, the breast is curved on one side and flat on the other side (wherein a flat slice on the flat side corresponds to the "curvature" of the breast), in the other case, the breast is curved at the top and bottom and the upper curvature bulges upward and the lower curvature bulges downward.

The intermediate slices should then form a transition from a curvature to a plane or between an upward curvature and a downward curvature (possibly with a flat slice in the middle).

Image reconstruction is basically known in the prior art. However, with the method described here no flat (planar) slice images are reconstructed, but rather slice images on the curved slices (wherein in particular one of these slices can also be flat, for example the middle slice of a biconvex breast or the outermost slice of a monoconvex breast). This results in essentially curved slice images.

Here, it should be noted that the slices are the theoretical planes by which the reconstruction is performed and the slice images are the ultimately reconstructed images.

The result image is then generated and output from these slice images as a slice stack, for example the slice images are simply placed one on top of the other.

Therefore, (curved) slice images are directly reconstructed in the recorded volume. The curvature can be based on the known curvature of the compression plate or the surface over the detector. This direct reconstruction has the advantage that it does not result in slices that are too short (planar).

An apparatus, according to an embodiment of the present invention, is used to generate a result image based on a tomosynthesis image dataset of a breast which is fixed by a compression plate to a detector, wherein the contact surface of the compression plate and/or detector facing the breast has a concave curvature. Herein, the apparatus is preferably designed to execute the method according to an embodiment of the present invention and comprises the following components:

- a slice unit designed to define curved slices between the compression plate and detector, which follow the curvature of the compression plate and/or detector in their shape or represent a transition between these curvatures,
- a reconstruction unit designed to reconstruct (curved) slice images lying on the curved slices
- a result unit designed to generate the result image as a slice stack of the (curved) slice images,
- a data interface designed to output the result image.

The function of the units has already been described above in the context of the method.

According to an embodiment of the present invention, an apparatus for generating a resultant image based on a tomosynthesis image dataset of a breast, which has been fixed to a detector by a compression plate, wherein a contact surface of at least one of the compression plate or the detector facing the breast has a concave curvature, comprises:

- a memory storing computer-executable instructions; and
- at least one processor configured to execute the computer-executable instructions to cause the apparatus to
  - define curved slices between the compression plate and the detector, each curved slice having a shape that follows a curvature of the at least one of the compression plate or the detector or that represents a transition between the curvature of the compression plate and the curvature of the detector,
  - reconstruct slice images lying on the curved slices,
  - generate the resultant image as a slice stack of the slice images, and
  - output the resultant image.

A mammography system, according to an embodiment of the present invention, comprises an apparatus according to an embodiment of the present invention and/or is designed to perform a method according to an embodiment of the present invention.

An embodiment of the present invention can in particular be implemented in the form of a computing unit, in particular in a control facility for a mammography system, with suitable software. For this purpose, the computing unit can, for example, have one or more interacting microprocessors or the like. In particular, it can be realized in the form of suitable software program parts in the computing unit. An extensively software-based implementation has the advantage that it is possible to retrofit computing units used to date in a simple way by a software update or firmware update in order to work in the manner according to embodiments of the present invention. In this respect, at least the object is also achieved by a corresponding non-transitory computer program product with a computer program, which can be loaded directly into a memory facility of a computing unit with program segments for executing all the steps of the method according to an embodiment of the present invention when the program is executed in the computing unit. In addition to the computer program, a computer program product can optionally comprise additional items, such as, for example, documentation and/or additional components, including hardware components, such as, for example, hardware keys (dongles etc.) for using the software. Transportation to the computing unit and/or storage on or in the computing unit can take place via a computer-readable medium, for example a memory stick, a hard disk or another portable or permanently installed data carrier on which the program segments of the computing unit that can be read-in and executed by the computer program are stored.

Further particularly advantageous embodiments and developments of the present invention emerge from the dependent claims and the following description, wherein the claims of one claim category can also be developed analogously to the claims and descriptive parts for another claim category and in particular individual features of different exemplary embodiments or variants can also be combined to form new exemplary embodiments or variants.

According to a preferred method, the curvature of a first slice, which is adjacent to the compression plate, substantially corresponds to the shape of the contact surface of the compression plate. As stated above, here "substantially" means that the curvature preferably corresponds to 80%, in particular 90%, of the curvature of the compression plate (for example the radius of curvature). Its curvature can be identical to the curvature of the compression plate, but if the first slice is somewhat remote from the compression plate, it is preferable for the curvature of the slice to be already slightly adapted to the opposite curvature.

According to a preferred method, the curvature of a second slice, which is adjacent to the detector, substantially corresponds to the shape of the contact surface of the detector. Likewise, here "substantially" means that the curvature preferably corresponds to 80%, in particular 90% of the curvature of the corresponding surface (for example the radius of curvature). Its curvature can be identical to the curvature of the surface, but if the second slice is somewhat remote from the surface, it is preferable for the curvature of the slice to be slightly adapted to the opposite curvature.

According to a preferred method, the curvature of one of the intermediate slices follows the shape of a regular transition between the curvature of the first slice and the second slice. Such a regular transition is, for example, a regular transition of the radii of curvature.

Preferably, the contact surface of the detector is flat and the second slice is likewise flat. The curvature of the further slices then preferably increases steadily from the second slice to the first slice.

According to a preferred method, the curvature of the first slice and/or the second slice is determined based on a measurement of the adjacent contact surface in each case. Since both the surface of the compression plate and the surface above the detector are known (or can be easily measured), this is easy to perform. It should be noted that the compressed breast follows these shapes and thus also the shape of the breast is known or can be easily determined.

According to a preferred method, the curvature of the first slice and/or the second slice is determined based on data from a sensor which measures the shape of the surface of the breast. This procedure has the advantage that errors in adapting the breast to the surfaces compressing it are avoided.

According to a preferred method, a coordinate system ($x_n$, $y_n$, $z_n$) is constructed for the curved slices in which the ($x_n$, $y_n$) in each case lie in a slice with the same n and the $z_n$ above the surface ($x_n$, $y_n$) specify the Z-position of the points of curved slice (i.e., the height above the detector). Thus, this coordinate system directly specifies the curved slices.

Specifically, the coordinates ($x_n$, $y_n$, $z_n$) can be calculated via a function F in a Cartesian coordinate system. In a simple example, ($x_n$, $y_n$) of a curved slice the (x, y) could correspond to a flat slice of a Cartesian coordinate system, i.e., $(x_n, y_n)=(x, y)$. Compared to this flat slice, the $Z_n$ of curved slice could be calculated from a specified function F, which defines the curvature. Herein, the slices can, for example, be calculated as follows:

$z_n=F_n(x, y)$ for individual functions $F_n$ for the individual slices, $z_n=F(x, y, n)$ for a common n-dependent function F for all slices, $z_n=F(x, y, z)$ for a z-dependent function F for all slices for selected values z, for example the z of the flat slices.

According to a preferred method, the reconstruction of slice images is based on a calculation of the paths of X-rays penetrating the curved slices. For a preferred projection of the slices, coordinate pairs are determined between a coordinate system $(x_n, y_n, z_n)$ and a coordinate system (x, y, z) in which a plurality of rays with the angles $(\alpha, \varphi)$ between points of intersection with the detector and the surface of the object are scanned in equidistant steps.

For this purpose, for the sake of clarity, it should be imagined that, when reconstructing slice images from a tomosynthesis image dataset (consisting, for example, of a plurality of projection images), in each case a voxel is assumed from which the voxel value is calculated from the tomosynthesis image dataset using known computing operations (in the Cartesian coordinate system). It is now possible to determine the position of each point $(x_n, y_n, z_n)$ of the curved slices in this Cartesian coordinate system. Therefore, the voxel value can also be calculated for each voxel at the position $(x_n, y_n, z_n)$. This provides all the required voxel values for the curved slices.

It should be noted that the X-ray beam is usually cone-shaped during recording. This should be taken into account during reconstruction. On the one hand, the conical shape means that a plurality of beams with different angles $(\alpha, \varphi)$ are emitted with each projection image of the tomosynthesis image dataset and that the beam intensity in a voxel of an upper slice is greater than that in a voxel of a lower slice. However, this can be compensated with correction calculations. These correction calculations are known in a Cartesian coordinate system. Here, it is likewise possible to determine the position of each point $(x_n, y_n, z_n)$ of the curved slices in this Cartesian coordinate system. Therefore, the correction calculation can also be carried out for each voxel at the position $(x_n, y_n, z_n)$. This provides all the required compensations for the curved slices. According to a preferred method, the reconstruction takes into account the conical shape of an X-ray beam to be recorded. Herein, the position of a plurality of points $(x_n, y_n, z_n)$ of the curved slices (in a Cartesian coordinate system) is determined and a correction calculation is carried out to compensate the conical shape of the X-ray beam for these points.

A special calculation or search (which should be optimized depending on the performance) can then be performed within the back projection loop based on the coordinate pairs. This calculation transforms a point in the coordinate system $(x_n, y_n, z_n)$ into a point in the coordinate system (x, y, z). In a Cartesian coordinate system, this can preferably take place via simple linear transformation.

According to a preferred method, therefore, a three-dimensional image of the breast in Cartesian coordinates is created as the result image. Herein, preferably image coordinates of the slice images are transformed into Cartesian coordinates via linear transformation.

According to a preferred method, the slices are aligned orthogonally to the surface normal of the contact surface of the detector. The slice images are then stacked in the direction of this surface normal to form the slice stack. This enables a very simple construction of the result image.

One or more embodiments of the present invention describe an advantageous sampling method that takes into account the shape of the breast and allows maximum benefit to be derived from the content of the slice images. It is also advantageous that the non-planar sampling geometries can be used directly for reconstruction. This avoids additional interpolation steps, which could, for example, impair the visibility of micro-calcifications.

BRIEF DESCRIPTION OF THE DRAWINGS

The present invention is explained again in more detail with reference to the accompanying figures and with reference to exemplary embodiments. Herein, the same components are given identical reference symbols in the various figures. The figures are generally not to scale. The figures show.

DETAILED DESCRIPTION

Figure 1:
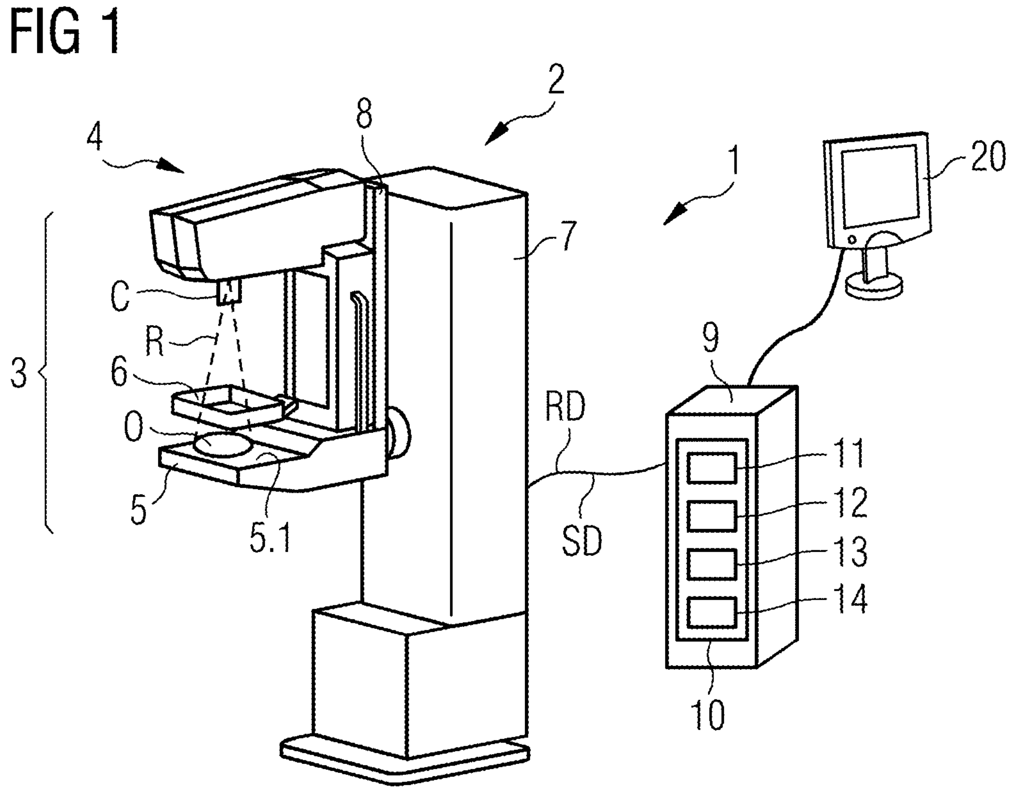
FIG. 1 a rough schematic depiction of a preferred mammography system with a preferred apparatus, FIG. 2 a flow chart for a possible sequence of a method according to an embodiment of the present invention, FIG. 3 an example of a compressed breast with a reconstruction with flat slices according to the prior art, FIG. 4 an example of a curved compressed breast with a reconstruction with flat slices according to the prior art, FIG. 5 an example of a curved compressed breast with a reconstruction with curved slices according to the method according to an embodiment of the present invention, FIG. 6 an example of a curved compressed breast with a reconstruction with curved slices according to the method according to an embodiment of the present invention.

FIG. 1 shows by way of example a rough schematic depiction of a mammography system 1 in the form of a tomosynthesis system 1. Relative directional indications such as “top”, “bottom” etc. refer to a tomosynthesis system 1 set up for operation as intended. The tomosynthesis system 1 comprises a tomosynthesis device 2 and a control facility 9.

The tomosynthesis device 2 has an upright column 7 and a source-detector arrangement 3, which in turn comprise an X-ray tube 4 and a detector 5 with a detector surface 5.1. In operation, the upright column 7 stands on the floor. The source-detector arrangement 3 is connected displaceably thereto so that the height of the detector surface 5.1, i.e., the distance to the floor, can be set to the height of a patient’s chest.

A breast O of the patient (here depicted schematically) lies on top of the detector surface 5.1 as the examination object O for an examination. A compression plate 6, which is displaceably connected to the source-detector arrangement 3 is arranged above the breast O and the detector surface 5.1. For the examination, the breast O is compressed and fixed at the same time by lowering the compression plate 6 onto it so that a pressure is exerted onto the breast O between the compression plate 6 and the detector surface 5.1. The contact surface of the compression plate 6 facing the breast has a concave curvature so that the breast is convexly curved there, as shown, for example, in FIGS. 4, 5 and 6.

The X-ray tube 4 is arranged and embodied opposite the detector 5 in such a way that the detector 5 captures the X-rays R emitted thereby when at least part of the X-rays R has penetrated the patient’s breast O. Herein, the X-ray tube 4 can be pivoted relative to the detector 5 by a rotating arm 8 in a range of ±50° about a basic position in which it is perpendicular to the detector surface 5.1. The section to be recorded can be specified or restricted by a collimator C.

The control facility 9 receives the raw data RD of the measurement and sends control data SD to the tomosynthesis device 2 via a data interface. It is connected to a terminal 20 via which a user can send instructions to the tomosynthesis system 1 or retrieve measurement results. The control facility 9 can be arranged in the same room as the tomosynthesis device 2, but it can also be located in an adjacent control room or at an even greater spatial distance.

Figure 2:
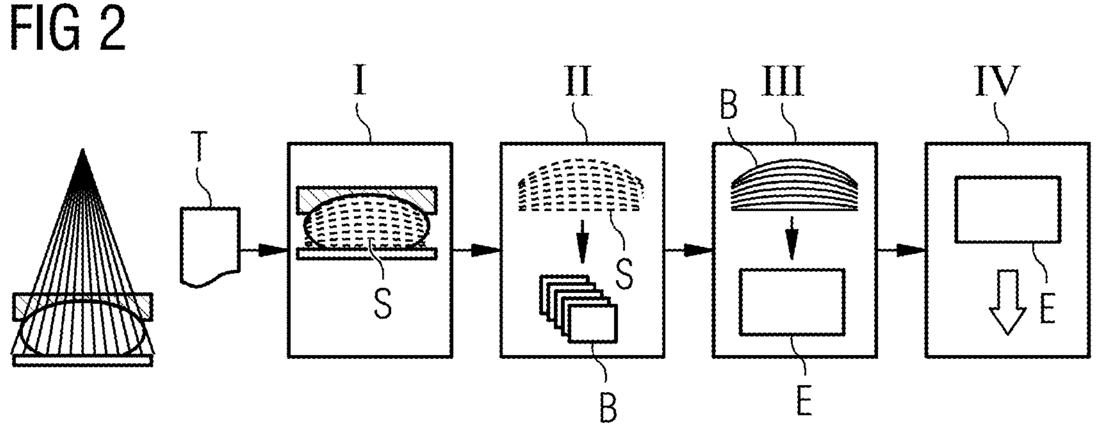

In this case, the apparatus 10, according to an embodiment of the present invention, for generating a result image based on a tomosynthesis image dataset of the breast is part of the control facility 9 and comprises a slice unit 11, a reconstruction unit 12, a result unit 13 and a data interface 14 (in this regard, see also the method according to FIG. 2).

The slice unit 11 defines curved slices S between the compression plate 6 and detector 5, which follow the curvature of the compression plate 6 and/or detector 5 in their shape or represent a transition between these curvatures. Such slices S are for example shown in FIGS. 5 and 6.

The reconstruction unit 12 is used to reconstruct slice images B, which lie on the curved slices S. The slice images B are therefore basically likewise curved and result in a section through the breast O along one of the slices S.

The result unit 13 then generates a result image E as a slice stack of the slice images B. For example, it arranges the slice images B in the form of a stack.

The result image E is then output via the data interface 14.

FIG. 2 shows a flow chart for a possible sequence of a method, according to an embodiment of the present invention, for generating a result image E based on a tomosynthesis image dataset T of a breast O, which has, for example, been recorded with the mammography system in FIG. 1. On the left, it is indicated how a compressed breast is recorded and the tomography dataset T is made available to the method.

In step I, curved slices S are defined between the compression plate 6 and detector 5, which follow the curvature of the compression plate 6 and/or detector 5 in their shape or represent a transition between these curvatures. Here, the regions in which the breast O was located during the recording O is of particular interest for the method.

In step II, slice images B lie on the curved slices S are then reconstructed. The reconstruction of slice images that follow slices is sufficiently well known. The special feature here is that, instead of flat slices (see for example FIGS. 3 and 4), curved slices S are assumed.

In step III, a result image E is created as a slice stack of the slice images B. Herein, the slices S are for example aligned orthogonally to the surface normal of the contact surface of the detector 5 (i.e., horizontally overall). The slice images B are stacked in the direction of the surface normal (i.e., here along the vertical) to form the slice stack.

This result image E is then output in step IV.

Figure 3:
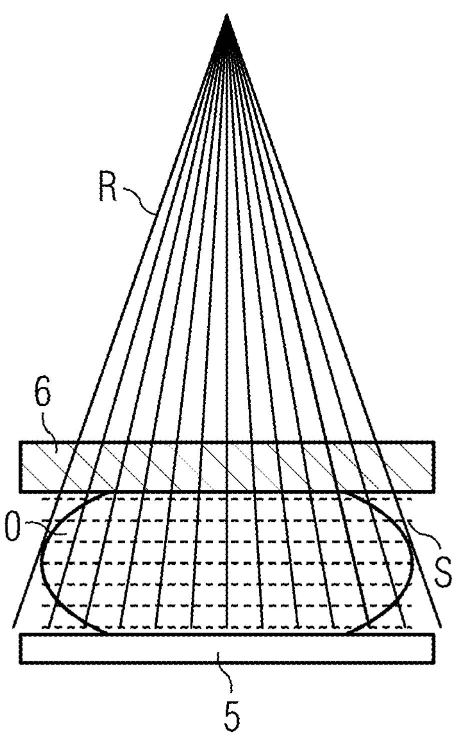
Figure 4:
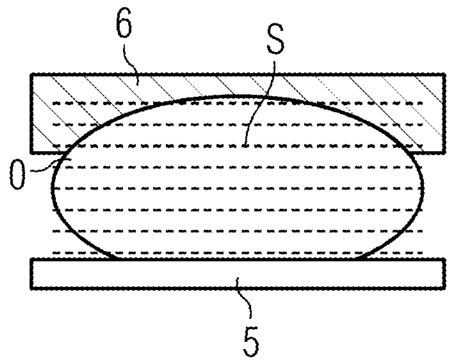

FIGS. 3 and 4 show an example of a compressed breast O with a reconstruction with flat slices according to the prior art.

Herein, FIG. 3 shows a breast O that is compressed by two flat surfaces. Here, the flat slices (dashed lines) are advantageous because they divide the space between the compression plate 6 and detector 5 evenly.

Figure 6:
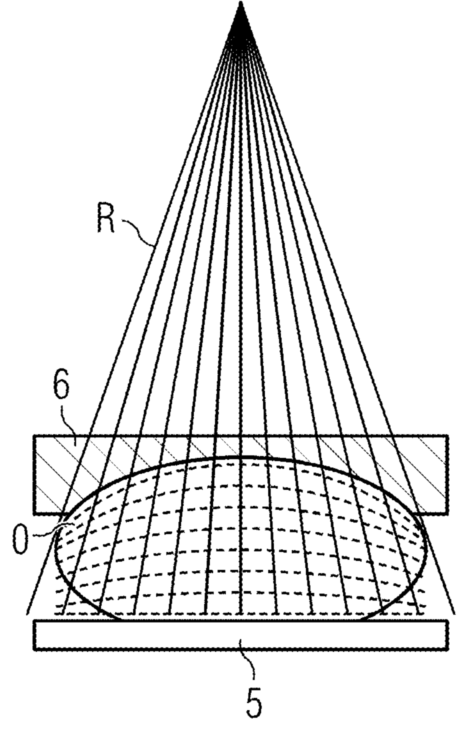

In contrast, the flat slices in FIG. 6, in which the breast O is compressed with a curved compression plate 6, are disadvantageous since they only affect a small part of the breast O at the top where the curvature is located. Therefore, reconstructed slice images B would only show a small slice of the breast O there.

Figure 5:
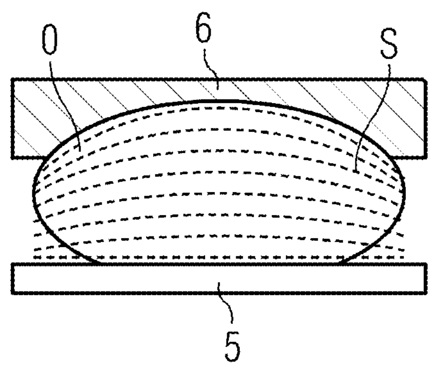

FIGS. 5 and 6 show an example of a curved compressed breast O with a reconstruction with curved slices S according to the method according to an embodiment of the present invention. Herein, the curvature of a first slice S (top), which is adjacent to the compression plate 6 substantially corresponds to the shape of the contact surface of the compression plate 6. The curvature of a second slice S (bottom), which is adjacent to the detector 5, substantially corresponds to the shape of the contact surface of the detector 5. The curvature of the intermediate slices S follows a regular transition between the curvature of the first slice S and the second slice S. Here, the contact surface of the detector 5 is flat and thus the second slice S is likewise flat.

Reference is made once again to the fact that the present invention described in detail above only entails exemplary embodiments, which can be modified by the person skilled in the art in a wide variety of ways without departing from the scope of the present invention. Furthermore, the use of the indefinite articles "a" or "an" does not preclude the possibility that the features in question may also be present on a multiple basis. Likewise, terms like "unit" do not preclude the possibility that the components in question may comprise a plurality of interacting sub-components, which could also be spatially distributed. The term "a number" should be understood as meaning "at least one".

Independent of the grammatical term usage, individuals with male, female or other gender identities are included within the term.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "inter faced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A method for generating a resultant image based on a tomosynthesis image dataset of a breast, which has been fixed to a detector by a compression plate, wherein a contact surface of at least one of the compression plate or the detector facing the breast has a concave curvature, and wherein the method comprises:

defining curved slices between the compression plate and the detector, each curved slice having a shape that follows a curvature of the at least one of the compression plate or the detector or that represents a transition between the curvature of the compression plate and the curvature of the detector;

reconstructing slice images that lie on the curved slices;

generating the resultant image as a slice stack of the slice images; and outputting the resultant image.

2. The method as claimed in claim 1, wherein a curvature of a first curved slice, which is adjacent to the compression plate, substantially corresponds to a shape of the contact surface of the compression plate, a curvature of a second curved slice, which is adjacent to the detector, substantially corresponds to a shape of the contact surface of the detector, a curvature of intermediate curved slices follows a regular transition between the curvature of the first curved slice and the curvature of the second curved slice, the second curved slice and the contact surface of the detector are flat, and the curvature of the intermediate curved slices increases steadily from the second curved slice to the first curved slice.

3. The method as claimed in claim 2, wherein the curvature of at least one of the first curved slice or the second curved slice is based on a measurement of an adjacent contact surface or based on data from a sensor that measures a shape of a surface of the breast.

4. The method as claimed in claim 1, further comprising:

Constructing a first coordinate system ($x_n$, $y_n$, $z_n$) for the curved slices, wherein coordinates ($x_n$, $y_n$) in each case lie in a curved slice at a same n, the $z_n$ above an area ($x_n$, $y_n$) specifies a position of points of the curved slice, coordinates ($x_n$, $y_n$, $z_n$) are calculated from a plurality of functions $F_n$ for individual slices, a function dependent on n, or a function dependent on z, and coordinates of points on flat slices are selected for z.

5. The method as claimed in claim 4, wherein the reconstructing of the slice images is based on a calculation of paths of X-rays penetrating the curved slices, and for a projection of the curved slices, coordinate pairs are determined between the first coordinate system ($x_n$, $y_n$, $z_n$) and a second coordinate system (x, y, z) in which a plurality of rays with angles ($\alpha$, $\varphi$) between points of intersection with the detector and a surface of the breast are scanned in equidistant steps.

6. The method as claimed in claim 4, wherein the reconstructing takes into account a conical shape of an X-ray beam, and the position of a plurality of points of the curved slices are determined and a correction calculation for compensating for the conical shape of the X-ray beam is carried out for the plurality of points.

7. The method as claimed in claim 1, wherein a three-dimensional image of the breast in Cartesian coordinates is created as the resultant image, and image coordinates of the slice images are converted into Cartesian coordinates via a linear transformation.

8. The method as claimed in claim 1, wherein the curved slices are aligned orthogonally to a surface normal of the contact surface of the detector and the slice images are stacked in a direction of the surface normal to form the slice stack.

9. An apparatus for generating a resultant image based on a tomosynthesis image dataset of a breast, which has been fixed to a detector by a compression plate, wherein a contact surface of at least one of the compression plate or the detector facing the breast has a concave curvature, and wherein the apparatus comprises:

a slice unit configured to define curved slices between the compression plate and the detector, each curved slice having a shape that follows a curvature of the at least one of the compression plate or the detector or that represents a transition between the curvature of the compression plate and the curvature of the detector;

a reconstruction unit configured to reconstruct slice images lying on the curved slices;

a resultant image generating unit configured to generate the resultant image as a slice stack of the slice images; and a data interface configured to output the resultant image.

10. A mammography system comprising the apparatus as claimed in claim 9.

11. A non-transitory computer program product comprising instructions that, when executed by a computer, cause the computer to execute the method as claimed in claim 1.

12. A non-transitory computer-readable storage medium comprising instructions that, when executed by a computer, cause the computer to execute the method as claimed in claim 1.

13. The method as claimed in claim 1, wherein a curvature of a first curved slice, which is adjacent to the compression plate, substantially corresponds to a shape of the contact surface of the compression plate, a curvature of a second curved slice, which is adjacent to the detector, substantially corresponds to a shape of the contact surface of the detector, and a curvature of intermediate curved slices follows a regular transition between the curvature of the first curved slice and the curvature of the second curved slice.

14. The method as claimed in claim 1, further comprising:

constructing a first coordinate system ($x_n$, $y_n$, $z_n$) for the curved slices, wherein coordinates ($x_n$, $y_n$) in each case lie in a slice at a same n, and the $z_n$ above an area ($x_n$, $y_n$) specifies a position of points of the curved slice.

15. The method as claimed in claim 1, further comprising:

Constructing a first coordinate system ($x_n$, $y_n$, $z_n$) for the curved slices, wherein coordinates ($x_n$, $y_n$) in each case lie in a slice at a same n, the $z_n$ above an area ($x_n$, $y_n$) specifies a position of points of the curved slice, and coordinates ($x_n$, $y_n$, $z_n$) are calculated via a specified function F.

16. The method as claimed in claim 1, further comprising:

constructing a first coordinate system ($x_n$, $y_n$, $z_n$) for the curved slices, wherein coordinates ($x_n$, $y_n$) in each case lie in a slice at a same n, the $z_n$ above an area ($x_n$, $y_n$) specifies a position of points of the curved slice, and coordinates ($x_n$, $y_n$, $z_n$) are calculated from a plurality of functions $F_n$ for individual slices, a function dependent on n, or a function dependent on z.

17. The method as claimed in claim 4, wherein the reconstructing of the slice images is based on a calculation of paths of X-rays penetrating the curved slices.

18. The method as claimed in claim 1, wherein a three-dimensional image of the breast in Cartesian coordinates is created as the resultant image.

19. A mammography system comprising an apparatus configured to perform the method as claimed in claim 1.

20. An apparatus for generating a resultant image based on a tomosynthesis image dataset of a breast, which has been fixed to a detector by a compression plate, wherein a contact surface of at least one of the compression plate or the detector facing the breast has a concave curvature, and wherein the apparatus comprises:

a memory storing computer-executable instructions; and at least one processor configured to execute the computer-executable instructions to cause the apparatus to define curved slices between the compression plate and the detector, each curved slice having a shape that follows a curvature of the at least one of the compression plate or the detector or that represents a transition between the curvature of the compression plate and the curvature of the detector, reconstruct slice images lying on the curved slices, generate the resultant image as a slice stack of the slice images, and output the resultant image.

* * * * *